United States Patent [19]

Segal

[11] Patent Number: 4,733,669

[45] Date of Patent: Mar. 29, 1988

[54] BLOOD FLOW MEASUREMENT CATHETER

[75] Inventor: Jerome Segal, San Mateo, Calif.

[73] Assignee: Cardiometrics, Inc., Mountain View, Calif.

[21] Appl. No.: 737,650

[22] Filed: May 24, 1985

[51] Int. Cl.[4] .............................................. A61B 10/00
[52] U.S. Cl. .................................... 128/663; 128/772; 604/96
[58] Field of Search ............... 128/663, 658, 656, 772, 128/4; 604/93, 96, 104, 105–107; 73/861.25, 151, 152

[56] References Cited

U.S. PATENT DOCUMENTS

| | | |
|---|---|---|
| 625,382 | 5/1899 | Clark . |
| 3,448,739 | 6/1969 | Stark et al. ........................ 128/2.05 |
| 3,554,030 | 1/1971 | Peronneau ........................ 128/663 |
| 3,566,682 | 3/1971 | Winkler, Jr. ......................... 73/152 |
| 3,580,983 | 5/1971 | Jackson ................................ 174/47 |
| 3,734,083 | 9/1970 | Kolin .................................. 128/2.05 |
| 3,746,003 | 7/1973 | Blake et al. ..................... 128/349 B |
| 3,865,118 | 2/1975 | Bures .................................. 128/404 |
| 3,935,864 | 2/1976 | Lagergren ........................... 128/418 |
| 3,938,530 | 2/1976 | Santomieri ..................... 128/349 R |
| 3,939,843 | 2/1976 | Smyth ................................ 128/404 |
| 3,995,623 | 12/1976 | Blake et al. ..................... 128/2.06 E |
| 4,029,104 | 6/1977 | Kerber ................................ 128/348 |
| 4,137,906 | 2/1979 | Akiyama et al. .................. 128/2 A |
| 4,299,226 | 11/1981 | Banka ................................ 128/344 |
| 4,328,806 | 5/1982 | Cooper ........................... 128/349 B |
| 4,329,993 | 5/1982 | Lieber ............................. 128/349 B |
| 4,329,994 | 5/1982 | Cooper ........................... 128/349 B |
| 4,354,500 | 10/1982 | Colley et al. ...................... 128/663 |
| 4,375,818 | 3/1983 | Suwaki et al. .......................... 128/4 |
| 4,407,271 | 10/1983 | Schiff ................................. 128/1 D |
| 4,448,195 | 5/1984 | LeVeen .............................. 128/344 |
| 4,545,244 | 10/1985 | Yasuda et al. .................... 73/861.25 |
| 4,582,067 | 4/1986 | Silverstein et al. ................ 128/663 |
| 4,584,874 | 4/1986 | Ruhovets .............................. 73/152 |

OTHER PUBLICATIONS

Martin et al, "An Ultrasonic Catheter for Intravascular Measurement of Blood Flow", Transactions on Sonics and Ultrasonics, vol. SU-27, No. 6, Nov. 1980, pp. 277–286.

Allen et al, "Integrated Circuits for a Bidirectional Implantable Pulsed Doppler Ultrasonic Blood Flowmeter", IEEE Journal of Solid State Circuits, vol. SC-13, No. 6, Dec. 1978, pp. 853–856.

"Catheter-Tip Gauge for Measuring Blood Flow Velocity and Vessel Diameter in Dogs," H. P. Piper & Lawrence T. Paul, *Journal of Applied Physiology*, vol. 24, No. 2, Feb. 1968.

"A Cathether-Tip Pressure and Velocity Sensor," H. F. Stegall, H. L. Stone & V. S. Bishop, 20th Annual Conf. on Engineering in Medicine & Biology, 11/15/67.

"Aortic Flow Velocity in Man During Cardiac Arrhythmias Measured with the Doppler Catheter–Flowmeter System," A. Benchimol, H. F. Stegall, P. R. Maroko, J. L. Gartlan, L. Brener; *American Heart Journal, tl vol. 78, No. 5, pp. 649–659, Nov. 1969.*

"A New Approach to Electromagnetic Blood Flow Determination by Means of Catheter in an External Magnetic Field," A. Kolin, *Proceedings of the National Academy of Sciences*, vol. 65, No. 3, pp. 521–527, Mar. 1970.

(List continued on next page.)

Primary Examiner—Edward M. Coven
Assistant Examiner—Ruth S. Smith
Attorney, Agent, or Firm—Flehr, Hohbach, Test, Albritton & Herbert

[57] ABSTRACT

A catheter having a mechanism for positioning a doppler shift transducer carried by the catheter against a side wall of a blood vessel. A portion of the catheter near the distal end is adjustable for movement between a first position in line with the axis of the catheter and a second position in which such catheter portion is in the shape of an arc extending outward from the axis of the catheter such that the arcuate portion will wedge the body of the catheter against the other wall of the blood vessel. The adjustable portion can be manipulated using a mechanism near the proximal end of the catheter outside of a patient's body.

32 Claims, 8 Drawing Figures

OTHER PUBLICATIONS

"An Electromagnetic Catheter Blood Flow Meter of Minimal Lateral Dimensions," A. Kolin, *Proceedings of the National Academy of Sciences,* vol. 66, No. 1, pp. 53–56, May 1970.

"A Removable Extraluminal Doppler Probe for Continuous Monitoring of Changes in Cardiac Output," B. A. Keagy, C. L. Lucas, H. S. Hsiao, B. R. Wilcox, *J. Ultrasound Medicine,* vol. 2, pp. 357–362, Aug. 1983.

"Bidirectional Blood Flow Velocity in the Cardiac Chambers and Great Vessels Studied with the Doppler Ultrasonic Flowmeter," A Benchimol, K. B. Desser, J. L. Gartlan, Jr.; *The American Journal of Medicine,* vol. 52, pp. 467–473, Apr., 1972.

"A Single-Crystal Ultrasonic Catheter-Tip Velocity Probe," G. J. Hartley & J. S. Cole, Medical Instrumentation, vol. 8, No. 4, Jul.–Aug., 1974, pp. 241–243.

"Totally Implantable Bidirectional Pulsed Doppler Blood Flow Telemetry: Integrated Timer–Exciter Circuitry and Doppler Frequency Estimation," H. B. Allen, Tech. Report No. 4958-4, PHS Research Grant PQ1 GM17940, pp. iii–147, May 1977.

"Totally Implantable Bidirectional Pulsed Doppler Blood Flow Telemetry: Integrated Ultrasonic Receiver, Diameter Detection, and Volume Flow Estimation," J. W. Knutti, Tech. Rept. No. 4958-5, PHS Research Grant P01 GM17940, pp. iii–iv, and Chapters I, II, III, pp. 66–80, 121–137, 151–165.

"The Pulsed Doppler Coronary Artery Catheter," J. S. Cole & C. J. Hartley; Circulation, vol. 56, No. 1, Jul. 1977.

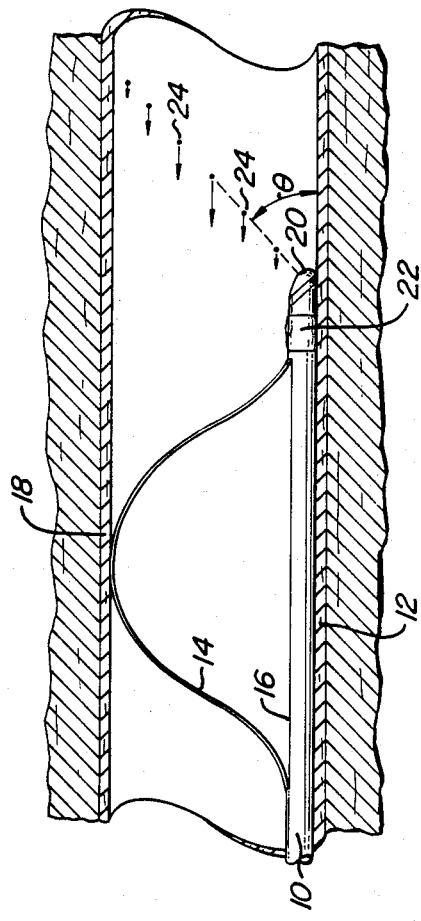
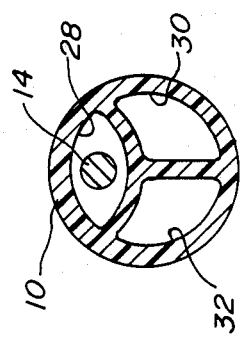
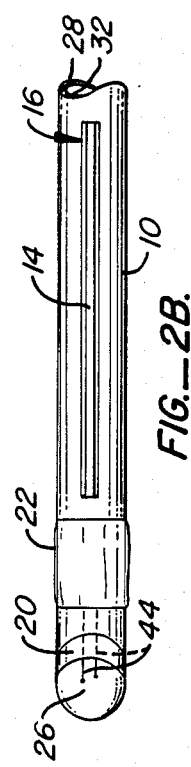
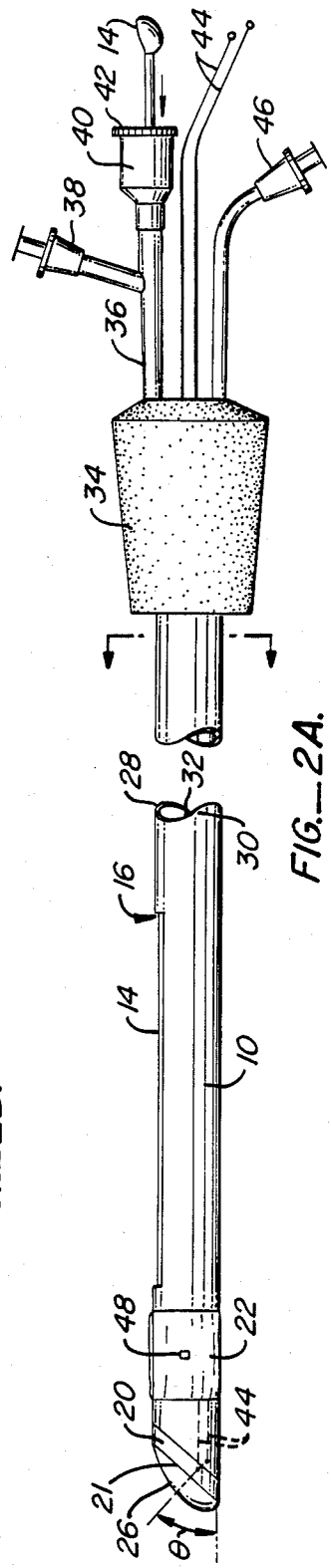

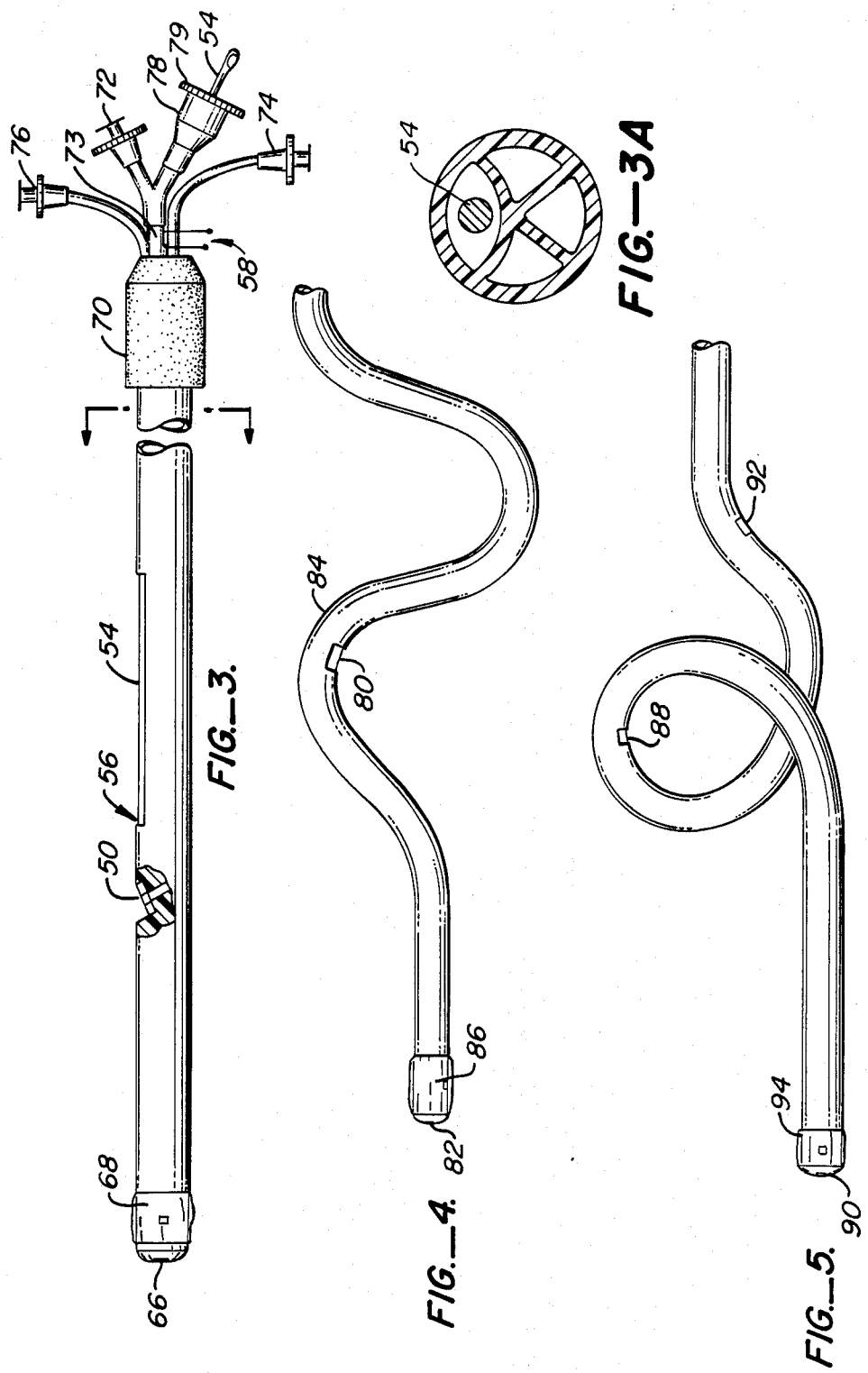

BLOOD FLOW MEASUREMENT CATHETER

BACKGROUND OF THE INVENTION

This invention relates to doppler catheters and, in particular, to an improved catheter adapted to measure instantaneous blood flow.

Blood flow measurements are useful as an indicator of the cardiovascular control mechanism that regulates flow to all organs and tissues. The measurement of blood flow allows an assessment of various interactions commonly used in modern medical practice to alter cardiac output and the functioning of the heart.

A catheter is an elongated tube-like device containing one or more hollow channels ("lumens") which is inserted into a blood vessel. Early catheters were developed to measure the pressure in an artery or vein. These catheters were filled with fluid allowing transmission of pressure from a hole at the catheter's tip ("distal" end) to a pressure measuring device ("manometer") at the end of the catheter outside the body (the "proximal" end). Later catheters incorporated one or more transducers at the distal end which would transmit a signal down the catheter lumen to a measuring device at the proximal end. These catheters were developed to measure volumetric blood flow and blood flow velocity.

A balloon wedge pressure catheter is used to measure pressures on the left side of the heart with a catheter inserted into the right side of the heart. This is done by advancing the catheter through the right side of the heart into the main pulmonary artery and into a pulmonary artery branch vessel. A balloon near the tip of the catheter is then inflated to block the vessel, thereby blocking pressures from the right side of the heart. The pressures measured by the tip of the catheter are that of the very distal pulmonary artery branch which is in direct communication with the pulmonary veins and which, in turn, reflect pressures on the left side of the heart.

Methods for measuring mean volumetric blood flow in man include thermal dilution, dye dilution, and "Fick" oxygen consumption methods. More recent devices have been developed to measure the instantaneous flow of blood in a vessel or artery. These include methods used to measure instantaneous flow by measuring changes in a concentric magnetic field across the blood vessel. To generate the concentric magnetic field requires either a cuff surgically placed around the vessel or a catheter precisely centered in the middle of the blood vessel.

One method for centering an electromagnetic-type catheter is to use an umbrella-like spring having a number of "V"-shaped spring elements with one end of the "V" coupled to the catheter and the other end coupled to a movable collar on the catheter. By moving the collar outwardly, the springs are made to expand and extend outward away from the catheter until the blood vessel walls are contacted. By using a number of these springs around the catheter, the catheter tip will be centered in the middle of the blood vessel. Such a centering device is disclosed in an article entitled "Registration of Phasic Changes of Bloodflow by Means of a Catheter-type Flow Meter," H. Piper, *The Review of Scientific Instruments*, Vol. 29, No. 11, p. 965 (November, 1958).

Techniques for measuring volumetric blood flow require the determination of the diameter of the blood vessel in order to determine the total volume of blood flow through the vessel itself. One method of determining the diameter is similar to the above-described centering device. A number of hinged braces near the end of a catheter tip are extended outwardly when a cuff to which they are attached slides along the catheter length. When these braces contact the blood vessel walls, a signal proportional to the diameter of the blood vessel is produced and sensed. Such a mechanism is disclosed in an article entitled "Catheter-Tip Gauge for Measuring Blood Flow Velocity and Vessel Diameter in Dogs," Piper and Paul, *Journal of Applied Physiology*, Vol. 24, No. 2, p. 259 (February, 1968).

Positioning problems may arise when a flow transducer is desired to be placed at the entrance to a small blood vessel branching off of a larger blood vessel. One method for accomplishing this involves attaching a wire to the end of the catheter similar to the bow string of a bow and arrow set. The transducer is placed at the center of that portion of the catheter directly opposite the wire that will be bowed. The catheter is then inserted into the main blood vessel until the transducer is adjacent to the entrance of the smaller blood vessel. The wire can then be pulled, thereby bowing the catheter and forcing the transducer against the entrance to the smaller blood vessel. See "An Electromagnetic Catheter-Flow Meter," Kolin and Archer, *Circulation Research*, p. 889 (December, 1967).

A doppler ultrasonic technique for measuring blood flow velocity uses a transmitter to transmit ultrasound across a blood vessel and a receiver to detect the change in frequency and phase shift of the reflected ultrasound signals. The measured frequency change is due to the movement of the blood cells which reflect the signals ("Doppler effect").

In one type of doppler flow meter ("continuous wave"), two transducers are used. One transducer continuously transmits ultrasound signals and the other continuously receives the reflected ultrasound signals. A weighting technique can then be used with readings from this type of doppler flow meter to determine the average velocity.

A pulsed-wave doppler technique uses a single crystal transducer with the received signal being sampled at certain specified intervals. These intervals correspond to different fixed positions across the blood vessel. The intervals are determined by the amount of time it takes the ultrasound wave to travel to a particular fixed position and return. Thus, the velocity at a series of points across the diameter of a blood vessel ("sample volumes") can be accurately and instantaneously determined.

The positioning of a pulsed-wave doppler transducer in a blood vessel is critical since the distribution of velocity across a vessel ("velocity profile") may not be uniform and a fixed reference is needed in order to measure these different velocities across the diameter of the entire blood vessel. The positioning of the catheter at the center of a blood vessel, as for electromagnetic transducers, is suboptimal because the doppler transducer measures velocity in a linear distribution resulting in the measurement of only the maximum velocity at the center of the blood vessel or some portion of the entire velocity profile. In order to determine the true volumetric rate of flow, the average velocity (obtained from the entire velocity profile) and vessel cross-sectional area (obtained from the vessel diameter) must be known. Both the velocity profile and diameter may be determined using a pulsed wave doppler transducer, if the transducer is placed along one vessel wall and the transmitted ultrasound signal is directed through the blood vessel diameter. One method of accomplishing this is through the use of an external collar containing the doppler transducer which is surgically implanted around the blood vessel. Such a collar is described in a Ph.D. dissertation by James Knutti of Stanford University entitled "Totally Implantable Bidirectional Pulsed Doppler Blood Flow Telemetry: Integrated Ultrasonic Receiver, Diameter Detection, and Volume Flow Estimation" (July, 1977).

In view of the limitations of known catheters, a need exists for an improved catheter having a positioning device for positioning the catheter intravenously against one of the walls of the blood vessel in which blood flow velocity is to be measured.

SUMMARY OF THE INVENTION

The present invention is directed to a catheter having a mechanism for positioning a doppler shift transducer carried by the catheter against a side wall of a blood vessel. A portion of the catheter near the distal end is adjustable for movement between a first position in line with the axis of the catheter and a second position in which such catheter portion is in the shape of an arc extending outward from the axis of the catheter such that the arcuate portion will wedge the body of the catheter against the opposite wall of the blood vessel. The adjustable portion can be manipulated using a mechanism near the proximal end of the catheter outside of a patient's body.

In one embodiment of the invention, the adjustable portion of the catheter is a pliable filament or wire which extends through the catheter and is exposed by a slot in the catheter near the distal end. After the catheter is inserted into the blood vessel, this wire is forced inwardly by a screw adjuster at the proximal end, causing the portion within the slot to bend and extend outwardly from the catheter body, thereby forming an arc. When the wire contacts one wall of the blood vessel, it thus forces the body of the catheter against the opposite wall of the blood vessel, thereby positioning the doppler shift transducer against such other wall of the blood vessel and aiming the ultrasound beam from such transducer through the center of the blood vessel diameter.

In another embodiment of the invention, the portion of the catheter near the distal end is preformed to define an arcuate shape, such as an "S" or a loop shape. A stiffening filament or wire inserted through a lumen in the catheter keeps the catheter straight while it is inserted into a blood vessel. After the catheter is in place, the stiffening wire is removed, allowing the catheter to assume its preformed shape, thus causing the catheter to be wedged against a side wall of the blood vessel. The transducer can either be placed on the body of the catheter at its tip or at the apex of the portion which is preformed in an arc.

In another embodiment of the invention, the transducer and arcuate portion of the catheter are located at a distance from the distal end of the catheter. The catheter can then be inserted through a vein, advanced through the right side of the heart and into the pulmonary artery in a manner similar to that previously described. A balloon between the distal end and the doppler shift transducer can then be inflated so that a pressure sensor on the distal tip of the catheter can sense pressures on the left side of the heart while the doppler shift transducer monitors blood flow on the right side of the heart.

For a fuller understanding of the nature and advantages of the invention, reference should be made to the ensuing detailed description taken in conjunction with the accompanying drawings.

BRIEF DESCRIPTION OF THE DRAWINGS

FIG. 1 is a side elevational view the distal extremity of a preferred embodiment of the catheter of the present invention in place in a blood vessel and showing a flexible elongate element forming a part of the catheter extended and engaging the vessel wall;

FIG. 2A is an enlarged and side elevational view of the preferred embodiment of the catheter showing the flexible elongate element retracted;

FIG. 2B is a top plan view of the distal extremity of the catheter shown in FIG. 1.

FIG. 2C is a cross sectional view taken along the line 2C—2C of FIG. 2A.

FIG. 3 is a side elevational view, similar to FIG. 2A, of another embodiment of the catheter of the present invention for the measurement of pressures on the left side of the heart;

FIG. 3A is a cross sectional view taken along the line 3A—3A of FIG. 3.

FIG. 4 is a side elevational view, of another embodiment of the present invention using a preformed "S"-shaped catheter body; and FIG. 5 is a side elevational view of a fourth embodiment of the present invention using a preformed loop-shaped catheter body.

DETAILED DESCRIPTION OF THE PREFERRED EMBODIMENT

FIGS. 2A and 2B show side and top views, respectively, of a catheter 10. Catheter 10 has a wire 14 which is exposed by a slot 16 near the distal end of the catheter. A transducer 20 is mounted at the distal end of catheter 10 and has a face 21 which is oriented so that a line perpendicular to the face defines an angle $\theta$ with the axis of catheter 10. Transducer 20 is covered by an epoxy or other coating 26. Catheter 10 has three lumens 28, 30, and 32. Wire 14 extends through lumen 28 to a proximal end 34 of catheter 10. Lumen 28 is coupled to an output tube 36 having a pair of ports 38 and 40. Proximal end of wire 14 extends through a channeled fitting of port 40. A nut 42 of port 40 can be rotated, thereby threading wire 14 into port 40 and moving wire 14 to the position shown in FIG. 1. Port 38 is coupled to a device outside the patient for measuring the pressure of the blood as sensed through slot 16. A pair of wires 44 at the distal end of catheter 10 are attached to transducer 20 and extend through the catheter, through lumen 32 and through proximal end 34. These wires 44 can be coupled to appropriate instrumentation for controlling doppler transducer 20. A port 46 is coupled to a lumen 30 which is connected to a hole 48 beneath latex balloon 22. Balloon 22 can be inflated by pumping air through port 46 along lumen 30 and out hole 48 to fill the balloon.

FIG. 1 shows a preferred embodiment of the catheter of the present invention in place in an artery. Catheter 10 is shown as being wedged against a side wall portion 12 of an artery. Wire 14 extends from slot 16 in catheter 10. Wire 14 engages and is wedged against a second side wall portion 18 of the artery. Doppler shift transducer 20 is located at the distal end of the catheter. Immediately behind transducer 20 is balloon 22 which can be inflated as needed. A series of points 24 indicate various positions ("sample volumes") within the artery at which the velocity of the blood will be measured by the catheter.

In operation, a series of short bursts of ultrasound waves or signals are emitted by transducer 20 along a line passing through points 24 along the vessel diameter. Points 24 are along a line which defines an angle $\theta$ relative to the axis of catheter 10 and the artery wall. The reflected waves or signals are sampled at a series of intervals corresponding to the round-trip transit times between transducer 20 and the positions 24. The blood flow velocity for each point 24 can then be determined by detecting the doppler frequency shift of the transmitted signal using known techniques. In addition, the direction of the blood flow can be determined by using two reference ultrasonic signals that are generated 90° out of phase with each other. The direction of the blood flow can then be determined from the phase shift of the reflected doppler signal as compared to the two reference signals in a conventional manner.

If the blood vessel is assumed to be circular in diameter, the velocity of the blood at each sample point 24 can be assumed to be the velocity at all points at an equal radius from the central axis of the blood vessel. To determine the flow volume per unit time of the blood vessel, the cross sectional area of the blood vessel and the average velocity across the blood vessel cross-section at any instant of time (the "space average velocity") can be calculated with the multiple of such area and velocity being the flow volume per unit time. The flow volume per unit time is thus given by:

$$\overset{\circ}{Q} = \bar{V} A$$

where
$\bar{V}$ = the space average velocity,
A = the cross sectional area in the plane perpendicular to the velocity vector, and
$\overset{\circ}{Q}$ = the volumetric flow per unit time. The space average velocity can be determined if the velocities calculated from the doppler shift frequency at a number of points 24 across the blood vessel are known. Each velocity point is weighted according to the corresponding area of concentric regions within the vessel.

The space average velocity is given by the following equation:

$$\bar{V} = \frac{1}{2N^2} \sum_{i=1}^{N} \{[v(r_i) + v(r_{-i})](2i - 1)\}$$

where:
$r_i$ = distance from center of blood vessel to concentric region at sample volume (point 24) position = i;
N = total number of points 24 measured; and
$v(r_i)$ = velocity measured at sample volume i at each of points 24 using the doppler shift frequency of the ultrasound beam emitted from transducer 20 at an angle $\theta$ to the main body axis of catheter 10.

The cross-sectional area of the artery can be determined from its diameter. The diameter can be determined with doppler transducer 20 by determining the point at which the blood flow velocity drops to zero in the artery. This point will be near the far wall 18 of the artery. This determination can be done continuously since the artery diameter and thus cross sectional area can vary as blood is pumped through it in bursts.

This cross-sectional area is given by the following equation:

$$A(t) = \frac{\pi d(t)^2}{4}$$

where:
A(t) = cross-sectional area as function of time; and
d(t) = diameter of blood vessel as function of time.
At any given instant of time, the following equation is true:

$$d = \frac{tr}{2c \sin \theta}$$

where:
d = true diameter of the blood vessel in a plane perpendicular to the axial velocity vector;
tr = transmit time for ultrasonic burst to traverse the blood vessel from transducer 20 to the opposite wall and return to transducer 20;
c = velocity of the ultrasound beam; and
$\theta$ = angle between the ultrasound beam and the vessel wall, or between a line perpendicular to face 21 of transducer 20 and the main body axis of catheter 10.

A feedback loop in the controlling circuitry (not shown) outside the patient's body can be used to adjust the positions of points 24 so that one point will always be positioned at far wall 18.

Catheter 10 of FIG. 1 preferably has a diameter of 2 mm and is made of a suitable flexible material, such as polyethylene. Catheter 10 may be inserted via the internal jugular vein or femoral vein and the latex balloon 22 can then be inflated with air. The balloon will extend across the flow of blood and will be advanced by the blood flow, pulling the catheter 10 along with it. The catheter may be advanced into the right atrium, through the tricuspid valve, the right ventricle, and the pulmonary valve with the doppler transducer 20 eventually being placed in the main pulmonary artery. The positioning of the catheter in the pulmonary artery may be confirmed either fluoroscopically or or by monitoring the pressure waveform transduced from slot 16 through lumen 28 connected to port 38 and coupled to a dynamic pressure sensing device (not shown).

A 6 MHz doppler crystal may, for example, be used as transducer 20. The crystal should be capable of determining velocity at eight to ten points 24 located at predetermined distances from the transducer 20. In operation, the returning doppler-shifted frequency signals are quadrature phase detected and compared to the original signal to determine the velocity and the direction of flow at a particular position 24. A real time two-dimensional velocity profile combining the eight to ten positions 24 may then be constructed using either a zero crossing counter or spectral analysis of the quadrature audio output of the transducer 20. The angle of incidence between the doppler ultrasound beam and the velocity vector of the blood, $\theta$, is known from the design of the catheter 10 because a line perpendicular to face 21 of transducer 20 is at a known angle, $\theta$, to the main body axis of catheter 10, which will be parallel to the velocity vector.

FIG. 3 shows another embodiment of the catheter of the present invention. A doppler transducer 50 is located at a point spaced from the distal end of the catheter. A wire guide 54 in a slot 56 is located immediately behind doppler transducer 50. The proximal end of wire guide 54 extends through a channeled fitting of port 78. A nut 79 of port 78 can be rotated, thereby threading wire 54 into port 78 and moving the wire into an arcuate position. An opening 66 at the distal end of the catheter provides a pressure measuring outlet. Immediately behind opening 66 is a balloon 68. A pair of wires 58 at the distal end at the catheter are attached to transducer crystal 50 and extend through the catheter through one of the lumens.

The proximal end 70 of the catheter has a number of ports, including two pressure ports 72 and 74. Pressure port 72 is coupled to output tube 73 which is coupled to port 78 and through one of four lumens to slot 56 to provide a pressure reading. Port 74 is coupled through another lumen to hole 66 to provide a distal pressure reading. Balloon 68 can be inflated, thereby blocking pressures from the right side of the heart and exposing hole 66 to pulmonary venous pressures which in turn reflect pressures on the left side of the heart while slot 56 will give pressure readings from the pulmonary artery and right side of the heart. The other ports are a balloon inflation port 76 and a port having guide wire adjustment screw 78.

In operation, the catheter of FIG. 3 may be advanced in a manner similar to a standard balloon wedge pressure catheter into the proximal pulmonary artery, through one of the main pulmonary artery branches, and into a distal pulmonary artery segment to the point at which the balloon becomes wedged in the artery. Distal hole 66 is now in communication with the pulmonary veins and may be used to measure pulmonary venous pressures. The proximal doppler crystal 50 may meanwhile be placed against the wall of the main pulmonary artery by advancing wire 54 into its arcuate position, wedged against a side wall portion of the artery in a manner similar to that described with reference to FIG. 1 above. Its position can be confirmed by monitoring the transduced pressure wave of the proximal pressure from slot 56 as observed at port 72. A velocity profile through the center of the pulmonary artery can then be obtained in the manner similar to that described with reference to FIG. 1 above. The advantage of this design is its ability to monitor both the instantaneous cardiac output along with pulmonary artery and pulmonary venous pressures.

FIG. 4 shows another embodiment of the present invention. The catheter of this embodiment is preformed into an S-shaped curve as indicated in the figure. A doppler crystal transducer 80 is located on the underside of the curve at approximately the apex thereof. A guide wire can be inserted through one of the four lumens to initially straighten the catheter for insertion into the venous system. The guide wire must be of sufficient strength to straighten the catheter and of sufficient flexibility to allow for ease of insertion of the catheter. The catheter is advanced as described above with respect to FIG. 3. Once in place, the guide wire is removed, allowing the catheter to assume its preformed shape. In this preformed shape, the portion of the catheter proximate transducer 80 will be wedged against a side wall of the artery. This catheter has a distal pressure hole 82 and a proximal pressure hole 84, as indicated. A balloon 86 is inflated to separate the two pressure holes 82, 84, as described with reference to FIG. 3, above.

Another embodiment of the present invention is shown in FIG. 5. In this embodiment the catheter is preformed into a spiral loop shape, as shown. Doppler crystal 88 is located at the apex of the loop. When in place in an artery, transducer 88 will be at the portion of the catheter wedged against a side wall of the artery. Because the loop is in a spiral, the portion of the loop opposite transducer 88 will not be in line with the transducer and thus will not interfere with the velocity measurements. This embodiment also contains distal pressure hole 90 and proximal pressure hole 92 along with a balloon 94. The operation of the catheter of FIG. 5 is similar to that for FIG. 4, above, using an internal guide wire to straighten the catheter on insertion with the guide wire being removed when the catheter is desired to be fixed in place.

The catheter of the present invention allows one to simultaneously measure instantaneous volumetric flow, blood vessel diameter, instantaneous velocity profile, and pulmonary artery pressure and/or pulmonary venous pressure. This combination of hemodynamic parameters will allow a physician to obtain a more accurate assessment of the patient's cardiovascular state at any time and the changes in such state with various physiological and pharmacological interventions. Mapping of the velocity profile of the major blood vessels may also provide the physician with a better understanding of the basic disease processes of these vessels and the heart in general.

As will be understood by those familiar with the art, the present invention may be embodied in other specific forms without departing from the spirit or essential characteristics thereof. For example, other shapes than those disclosed in FIGS. 4 and 5 could be used, or a three-lumen catheter could be used in place of the four-lumen catheter by removing one of the functions, or more lumens could be added. Alternative means of calculating volumetric flow utilizing information concerning doppler frequency shift and vessel diameter, obtained from the doppler transducer, could also be employed. Accordingly, the disclosure of the preferred embodiments of the present invention is intended to be illustrative, but not limiting, of the scope of the invention which is set forth in the following claims.

What is claimed is:

1. A catheter comprising an elongate body for extending through a blood vessel to a proximal end exterior of a person's body, said elongate body having proximal and distal extremities;

an elongate portion of said body near the distal extremity thereof being movable between a first position substantially parallel to the axis of said body and a second position along an arcuate path having an apex and extending outwardly from said first position;

means carried by said body for causing movement of said elongate portion between said first position and said second position, so that in said second position, said elongate portion contacts a side wall of said blood vessel and forces said body against an opposite side wall of said blood vessel and a transducer carried by said elongate body and positioned proximate a side wall of said blood vessel when said elongate portion is in said second position.

2. The apparatus of claim 1 wherein said elongate portion includes an axial slot in the elongate body and a pliable filament carried by the elongate body and being disposed within said body in said first position of said elongate portion and being moveable through said axial slot in said second position of said elongate portion.

3. The apparatus of claim 2 wherein said slot is located such that said transducer is between said slot and said distal end of said elongate body.

4. The apparatus of claim 1 wherein said transducer is mounted on the distal end of said elongate body.

5. The apparatus of claim 1 wherein said transducer is mounted on said elongate body at a position spaced apart from the distal end thereof.

6. The apparatus of claim 1 further comprising an inflatable balloon near said distal end.

7. The apparatus of claim 1 wherein said transducer is located on said elongate portion so that said transducer will be positioned near an apex of said arcuate path when said elongate portion is in said second position.

8. The apparatus of claim 7 wherein said elongate body is preformed to assume said second position and wherein said means for causing movement includes a pliable filament internal to said elongate body, said pliable filament holding said elongate body in said first position when the elongate body is in place in a blood vessel, said elongate body assuming said second position when said pliable filament is removed.

9. The apparatus of claim 8 wherein said elongate portion is "S"-shaped.

10. The apparatus of claim 9 further comprising a pressure hole located at said distal end of said elongate body.

11. The apparatus of claim 9 further comprising a second pressure hole proximate to said transducer.

12. The apparatus of claim 9 further comprising an inflatable balloon near said distal end.

13. The apparatus of claim 8 wherein said elongate portion comprises a 360° spiral loop.

14. The apparatus of claim 13 further comprising a pressure hole located at the distal end of said elongate body.

15. The apparatus of claim 13 further comprising a second pressure hole located proximate to said transducer.

16. The apparatus of claim 13 further comprising an inflatable balloon near said distal end.

17. A catheter comprising:
an elongate body for extending into a blood vessel, said elongate body having proximal and distal extremities;
a pliable filament disposed within said elongate body, said elongate body having an axially extending slot therein, said pliable filament being adjustable between a first position within said slot and a second position along an arcuate path extending outward from said first position and from said slot, a transducer carried by said elongate body near the distal extremity thereof and
means near said proximal extremity of said elongate body for adjusting said pliable filament between said first position and said second position so that in said second position, said pliable filament contacts a side wall of said blood vessel and forces said elongate body against an opposite side wall of said blood vessel so that said transducer is positioned near a side wall of said blood vessel.

18. A catheter as in claim 17 wherein said transducer is coupled to the distal end of said elongate body.

19. A catheter as in claim 17 wherein said transducer is coupled to said elongate body at a position spaced apart from said distal end thereof.

20. A catheter as in claim 17 wherein said filament is a wire.

21. A catheter comprising:
an elongate catheter body, for extending through a blood vessel to a proximal end exterior of a person's body;
a transducer coupled to a distal end of said catheter body;
a pliable filament disposed within an axial slot within said catheter body, said slot being located such that said transducer is located between said slot and said distal end, said pliable filament being adjustable between a first position within said slot and a second position along an arcuate path extending outward from said first position;
means near said proximal end of said body, for adjusting said pliable filament between said first position and said second position;
an inflatable balloon coupled to said catheter between said transducer and said distal end;
a pressure hole proximate said distal end;
whereby, in said second position, said pliable filament contacts a side wall of said blood vessel, thereby forcing said catheter body against an opposite side wall of said blood vessel so that said transducer can be positioned near a side wall of said blood vessel, said balloon being inflatable to block said blood vessel so that said pressure hole can monitor a pressure isolated from said transducer.

22. A catheter comprising:
an elongate body for extending through a blood vessel from a proximal end exterior of a person's body to a distal end in a blood vessel;
a pliable portion of said body near said distal end, said pliable portion being preformed in a first position along an S-shaped arcuate path extending outward from said elongate body;
a pliable filament internal to said elongate body, said filament holding said pliable portion in a second position substantially parallel to the axis of said elongate body, said pliable portion assuming said first position when said filament is removed; and
a transducer coupled to said pliable portion proximate an apex of said S-shaped arcuate path;
whereby, in said first position, said pliable portion contacts a side wall of said blood vessel, thereby forcing said elongate body against an opposite side wall of said blood vessel so that said transducer can be positioned proximate a side wall of said blood vessel.

23. The apparatus of claim 22 further comprising a pressure hole near said distal end of said elongate body.

24. The apparatus of claim 23 further comprising an inflatable balloon intermediate said pressure hole and said transducer.

25. A catheter comprising:
an elongate body for extending through a blood vessel from a proximal end exterior of a person's body to a distal end in a blood vessel;
a pliable portion of said body near said distal end, said pliable portion being preformed in a first position along a 360° spiral loop arcuate path extending outward from said elongate body;
a pliable filament internal to said elongate body, said filament holding said pliable portion in a second position substantially parallel to the axis of said elongate body, said pliable portion assuming said first position when said filament is removed; and transducer coupled to said pliable portion proximate an apex of said 360° spiral loop arcuate path;

whereby, in said first position, said pliable portion contacts a side wall of said blood vessel, thereby forcing said elongate body against an opposite side wall of said blood vessel so that said doppler shift transducer can be positioned proximate a side wall of said blood vessel.

26. The apparatus of claim 25 further comprising a pressure hole near said distal end of said elongate body.

27. The apparatus of claim 26 further comprising an inflatable balloon intermediate said pressure hole and said transducer.

28. In a device for making measurements in a blood vessel, a flexible elongate element adapted to be inserted into the blood vessel and having a plurality of lumens extending longitudinally thereof, said elongate element having proximal and distal ends, a transducer carried by the elongate element and means carried by the elongate element for causing a portion of the elongate element to be urged against the wall of the blood vessel so that it remains in a relatively fixed position during pulsatile flow of blood through the blood vessel, said transducer being disposed in relatively close proximity to said portion whereby said portion provides a desired orientation for the transducer.

29. A device as in claim 28 together with inflatable balloon means carried by the elongate element near the distal extremity thereof and having the interior thereof in communication with one of said lumens.

30. A device as in claim 29 wherein the means carried by the element for causing said portion of said elongate element to be urged against the wall of the blood vessel includes a flexible member extending through at least a portion of another of said lumens.

31. A device as in claim 30 wherein said elongate element is formed with a slot therein extending longitudinally thereof and wherein a portion of said flexible member extends through said slot causing said portion to be urged against the wall of the vessel.

32. A device as in claim 28 wherein said transducer is an ultrasonic transducer and wherein said orientation of said transducer is such that the ultrasonic energy emanating from said transducer passes through a central longitudinal axis of the blood vessel.

* * * * *